(12) United States Patent
Suyasu et al.

(10) Patent No.: US 9,045,406 B2
(45) Date of Patent: Jun. 2, 2015

(54) PROCESS FOR PRODUCING ALKYL METHACRYLATE

(71) Applicant: SUMITOMO CHEMICAL COMPANY, LIMITED, Chuo-ku, Tokyo (JP)

(72) Inventors: Noriaki Suyasu, Niihama (JP); Eiichi Shiraishi, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 35 days.

(21) Appl. No.: 13/840,286

(22) Filed: Mar. 15, 2013

(65) Prior Publication Data
US 2013/0261335 A1 Oct. 3, 2013

(30) Foreign Application Priority Data

Mar. 27, 2012 (JP) ................................. 2012-071298

(51) Int. Cl.
*C07C 51/25* (2006.01)
(52) U.S. Cl.
CPC ..................... *C07C 51/252* (2013.01)
(58) Field of Classification Search
CPC ..................................................... C07C 51/25
USPC ....................................................... 562/534
See application file for complete search history.

(56) References Cited

U.S. PATENT DOCUMENTS 4,303,550 A * 12/1981 Callahan et al. ................ 502/24

FOREIGN PATENT DOCUMENTS

| JP | 55-124734 | * | 9/1980 |
| JP | 55-124734 A | | 9/1980 |
| WO | 2010-052909 A1 | | 5/2010 |

* cited by examiner

*Primary Examiner* — Yong Chu
*Assistant Examiner* — Sonya Wright
(74) *Attorney, Agent, or Firm* — Sughrue Mion, PLLC

(57) ABSTRACT

An object of the present invention is to provide a process for producing methacrylic acid with good productivity over a long period of time.
The present invention provides a process for producing methacrylic acid by oxidizing methacrolein with oxygen in a continuous manner, comprising supplying a mixed gas containing methacrolein, isobutylene and oxygen and having a content of isobutylene of 300 to 3000 volume ppm, initiating the oxidation so that the methacrolein conversion at an outlet of a reactor becomes at least 85% and, thereafter, continuing the oxidation while the mixed gas having a content of isobutylene of 300 to 3000 volume ppm is supplied until a difference (X1−X2) between methacrolein conversion (X2) at the outlet of the reactor and methacrolein conversion (X1) at the outlet of the reactor at the time of the initiation of oxidation comes into the range of 2 to 30%, and continuing the oxidation while the mixed gas having a content of isobutylene of 500 volume ppm or less is supplied, after the difference (X1−X2) comes into the range of 2 to 30%.

8 Claims, No Drawings

PROCESS FOR PRODUCING ALKYL METHACRYLATE

BACKGROUND OF THE INVENTION

1. Field of the Invention

The present application claims the Paris Convention priority based on Japanese Patent Application No. 2012-71298 filed on Mar. 27, 2012, the entire content of which is incorporated herein by reference.

The present invention relates to a process fox producing methacrylic acid.

2. Description of the Related Art

As one of processes for producing methacrylic acid, there is known a process of subjecting methacrolein to vapor phase catalytic oxidation with molecular oxygen in the presence of a catalyst. For example, Patent Document 1 (JP-A-2005-272313) describes a process of performing initial operation at a reaction temperature or 290° C. or higher and 310° C. or lower and, thereafter, performing steady operation at a reaction temperature of 270° C. or higher and lower than 290° C., when in ethacrylic acid is produced by oxidizing methacrolein in a mixed gas containing methacrolein and oxygen, with oxygen, in a continuous manner, by extracting a reaction mixture from a reactor containing a catalyst for producing methacrylic acid while supplying the mixed gas into the reactor.

Patent Document 1: JP-A-2005-272313

SUMMARY OF THE INVENTION

However, the aforementioned process is not necessarily satisfactory in respect of durability of the catalyst activity, and a process capable of producing methacrylic acid with good productivity over a further longer period of time has been desired.

Thus, an object of the present invention is to provide a process for producing methacrylic acid with good productivity over a long period of time.

In order to achieve the aforementioned object, the present inventors intensively studied and, as a result, completed the present invention.

That is, the present invention includes the following embodiments.

[1] A process for producing methacrylic acid including oxidizing methacrolein in a mixed gas containing methacrolein, isobutylene and oxygen, with oxygen, in a continuous manner, by extracting a reaction mixture from a reactor containing a catalyst for producing methacrylic acid, while supplying the mixed gas into the reactor, wherein the mixed gas having a content of isobutylene of 300 to 3000 volume ppm is supplied, and the oxidation is initiated so that the methacrolein conversion at an outlet of the reactor becomes at least 85%, thereafter, the oxidation is continued while the mixed gas having a content of isobutylene of 300 to 3000 volume ppm is supplied, until a difference (X1–X2) between methacrolein conversion (X2) at the outlet of the reactor and methacrolein conversion (X1) at the outlet of the reactor at the initiation of oxidation comes into the range of 2 to 30%, and the oxidation is continued while the mixed gas having a content of isobutylene of 500 volume ppm or less is supplied, after the difference (X1–X2) comes into the range of 2 to 30%, provided that the case is excluded where the oxidation is continued while the mixed gas having a content of isobutylene of 300 to 500 volume ppm is supplied, in both of the period until the difference (X1–X2) comes into the range of 2 to 30% from the initiation of oxidation, and after the difference (X1–X2) comes into the range of 2 to 30%.

[2] The process according to wherein the oxidation is performed so that the reaction temperature for a period during which the difference (X1–X2) comes into the range of 2 to 30% after the initiation of oxidation comes into the range of ±5° C. relative to the reaction temperature at the time of the initiation of oxidation.

[3] The process according to [1] or [2], wherein the content of methacrolein in the mixed as is 2.5 to 5.0 volume %.

[4] The process according to any one of [1] to [3], wherein the mixed gas is a reaction gas obtained by oxidizing isobutylene in a mixed gas containing isobutylene and oxygen, with oxygen, in the presence of a catalyst for producing methacrolein, or a gas obtained by mixing the reaction gas with at least one gas selected from the group consisting of methacrolein, isobutylene, oxygen and an inert gas.

[5] The process according to any one of [1] to [4], wherein the reactor is a fixed bed reactor.

[6] The process according to any one of [1] to [5], wherein the catalyst for producing methacrylic acid is made of a heteropolyacid compound containing phosphorus and molybdenum.

[7] The process according to [6], wherein the heteropolyacid compound further contains vanadium, at least one element selected from the group consisting of potassium, rubidium, cesium and thallium, and at least one element selected from the group consisting of copper, arsenic, antimony, boron, silver, bismuth, iron, cobalt, lanthanum and cerium.

[8] The process according to any one of [4] to [7], wherein the catalyst for producing methacrolein is made of a complex oxide containing molybdenum, bismuth and iron.

According to the present invention, methacrylic acid can be obtained with good productivity over a long period of time.

DETAILED DESCRIPTION OF THE INVENTION

The present invention will be explained, in detail below.

The catalyst for producing methacrylic acid used in the present invention is not particularly limited, but a catalyst made of a heteropolyacid compound containing phosphorus and molybdenum is preferable. The heteropolyacid compound constituting the catalyst may be free heteropolyacid or a salt of heteropolyacid. Among them, an acidic salt (partially neutralized salt) of heteropolyacid is preferable, and an acidic salt of Keggin type heteropolyacid is further preferable.

It is desirable that the catalyst for producing methacrylic acid contains vanadium as an element other than phosphorus and molybdenum, and it is desirable that the catalyst contains at least one element (hereinafter, sometimes referred to as element X) selected from the group consisting of potassium, rubidium, cesium and thallium, and at least one element (hereinafter, sometimes referred to as element Y) selected from the group consisting of copper, arsenic, antimony, boron, silver, bismuth, iron, cobalt, lanthanum and cerium. Usually, a catalyst containing phosphorus, vanadium, the element X and the element Y respectively at a ratio of 3 atoms or less relative to 12 atoms, of molybdenum is suitably used.

A preferable composition of the heteropolyacid compound constituting the catalyst for producing methacrylic acid obtained in the present invention is as in the following formula (i).

$$P_a Mo_b V_c X_d Y_e O_x \qquad (i)$$

wherein P, Mo and V each represent phosphorus, molybdenum and vanadium, X represents at least one element X selected from the group consisting potassium, rubidium, cesium and thallium, Y represents at least one element Y selected from the group consisting of copper, arsenic, antimony, boron, silver, bismuth, iron, cobalt, lanthanum and cerium, O represents oxygen, when b=12, $0<a\leq 3$, $0\leq c\leq 3$, $0\leq d\leq 3$, and $0\leq e\leq 3$ are satisfied, and x is a value determined by the oxidation state of each element. In addition, when each of X and Y is two or more elements, the total ratio of the two or more elements should satisfy $0<d\leq 3$ and $0<e\leq 3$ when b=12.

As a raw material for obtaining the catalyst for producing methacrylic acid, usually, compounds containing elements contained in the heteropolyacid compound, for example, an oxo acid, an oxo acid salt, an oxide, a nitrate, a carbonate, a bicarbonate, a hydroxide, a halide, and an amine complex of the elements are used at a ratio satisfying a desired atomic ratio. As the compound containing phosphorus, phosphoric acid, a phosphate and the like are used, as the compound containing molybdenum, molybdic acid, a molybdate such as ammonium molybdate, molybdenum oxide, molybdenum chloride and the like are used, and as the compound containing vanadium, vanadic acid, a vanadate (metavanadate) such as ammonium vanadate (ammonium metavanadate), vanadium oxide, vanadium chloride and the like are used. As the compound containing the element X, oxides such as potassium oxide, rubidium oxide, and cesium oxide; nitrates such as potassium nitrate, rubidium nitrate, cesium nitrate, and thallium nitrate; carbonates such as potassium carbonate, rubidium carbonate, and cesium carbonate; bicarbonates such as potassium bicarbonate and cesium bicarbonate; hydroxides such as potassium hydroxide, rubidium, hydroxide, and cesium hydroxide; and halides such as potassium chloride, rubidium chloride, cesium fluoride, cesium chloride, cesium bromide, and cesium iodide are used. As the compound containing the element Y, an oxo acid, an oxo acid salt, a nitrate, a carbonate, a hydroxide, a halide and the like are used.

The process for producing the catalyst for producing methacrylic acid is not particularly limited, and examples thereof include a process of subjecting a catalyst precursor prepared from the catalyst raw materials to calcination. This catalyst precursor can be usually prepared by mixing the catalyst raw materials in water to obtain an aqueous solution or an aqueous slurry and, then, drying this aqueous mixed liquid. The precursor may be, for example, a precursor obtained by molding the dried material, a precursor obtained by heat-treating the dried material (pre-calcination) and molding the material, or a precursor obtained by molding the dried material and heat-treating the material. Herein, the method of drying the aqueous mixed liquid is not particularly limited, and a method usually used in this field, such as evaporation to dryness, a spray drying method, a drum drying method, and an air flow drying method can be adopted. Among them, the drying is preferably performed by a spray drying method using a spray drier or the like. The molding may be performed by a method usually used in this field, such as compression molding or extrusion molding, and examples of the shape after molding include a ring shape, a pellet shape, a spherical shape, and a cylindrical shape. Upon molding, if necessary, water, a molding aid, a pore forming agent or the like can be added to the dried material. Examples of the molding aid include ammonium nitrate, in addition to a ceramic fiber and a glass fiber. Particularly, ammonium nitrate has not only the function as the molding aid, but also the function as the pore forming agent.

As the method of preparing the catalyst precursor, it is desirable that an ammonium compound is used as a catalyst raw material, or ammonia or an ammonium salt is added to obtain an aqueous mixed liquid containing an ammonium radical, the liquid is dried and, thereafter, heat-treated and then molded, or molded and then heat-treated. According to these formulations, upon heat treatment, a structure of Keggin type heteropolyacid salt can be formed, and a catalyst precursor made of the thus obtained Keggin type heteropolyacid salt is particularly suitable for calcination described later.

It is preferable that a molded product obtained by the molding is subsequently subjected to temperature and humidity control treatment. Specifically, the temperature and humidity control treatment is performed by exposing the molded product to an atmosphere of 4.0 to 100° C. and a relative humidity of 10 to 60% for around 0.5 to 10 hours. The treatment may be performed in a tank which has been temperature-and-humidity-controlled, or may be performed by blowing a temperature-and-humidity-controlled gas to the molded product, for example. As an atmosphere gas when the treatment is performed, usually the air is used, but an inert gas such as nitrogen may also be used.

It is desirable that heat treatment after drying or molding is performed at a temperature around 180 to 300° C. under an atmosphere of an oxidizing gas or a non-oxidizing gas.

The thus obtained catalyst precursor is subjected to calcination. The calcination method is not particularly limited and calcination can be performed by a method usually used in this field. For example, calcination may be performed under an atmosphere of an oxidizing gas such as oxygen, or may be performed under an atmosphere of a non-oxidizing gas such as nitrogen, and the calcination temperature is usually 300° C. or higher. Among them, in respect that a catalyst for producing methacrylic acid having a good catalyst life is obtained, it is preferable to perform multi-stage calcination under art atmosphere of an oxidizing gas or a non-oxidizing gas, and it is more preferable to adopt a two-stage calcination method, in which first stage calcination is performed under an atmosphere of an oxidizing gas and, then, second stage calcination is performed under an atmosphere of a non-oxidizing gas.

The oxidizing gas used in calcination is a gas containing an oxidizing substance, and examples thereof include an oxygen-containing gas. When an oxygen-containing gas is used, the oxygen concentration thereof should be usually around 1 to 30 volume %, and as an oxygen source, usually, the air or pure oxygen is used and, if necessary, the gas is diluted with an inert gas. In addition, in the oxidizing gas, moisture may be present as necessary, and the concentration thereof is usually 10 volume % or lower. Among them, as the oxidizing gas, the air is preferable. Calcination performed under the oxidizing gas atmosphere is usually conducted under a stream of such an oxidizing gas. The temperature for calcination performed under the oxidizing gas atmosphere is usually 360 to 410° C., preferably 380 to 400° C.

The non-oxidizing gas used in calcination is a gas containing substantially no oxidizing substance such as oxygen, and examples thereof include inert gases such as nitrogen, carbon dioxide, helium, and argon. In addition, moisture may be present in the non-oxidizing gas as necessary and the concentration thereof is usually 10 volume % or lower. As the non-oxidizing gas, inter alia, nitrogen is preferable. Calcination performed under the non-oxidizing gas atmosphere is usually conducted under a stream of such a non-oxidizing gas. The temperature for calcination performed under the non-oxidizing gas atmosphere is usually 420 to 500° C., and preferably 420 to 450° C.

When these calcination temperatures are lower than predetermined values, the activity of the resulting catalyst may become insufficient or the catalyst life may be insufficient. On the other hand, when these calcination temperatures exceed predetermined values, since the catalyst is easily degraded and sintered, the activity of the resulting catalyst may become insufficient. The time for each calcination is each appropriately adjusted, and is usually around 1 to 20 hours. It is desirable that each calcination is performed while flowing a gas used as an atmosphere gas.

The process for producing methacrylic acid of the present invention is to oxidize methacrolein in a mixed gas containing methacrolein, isobutylene and oxygen, with oxygen, in a continuous manner, by extracting a reaction mixture from a reactor containing the catalyst for producing methacrylic acid, while supplying the mixed gas to the reactor.

As a reaction system, reaction systems such as a fluidized bed, a fixed bed, and a moving bed can be adopted, and it is desirable from the viewpoint of productivity and operability to perform the reaction by a fixed bed flowing system in which the mixed gas is flowed through a fixed bed reactor filled with the catalyst for producing methacrylic acid. A reaction by the fixed bed flowing system can be performed by, for example, passing the mixed gas through the fixed bed reactor filled with the catalyst for producing methacrylic acid by upflow or downflow. In addition, as the fixed bed reactor, various fixed bed reactors of flowing system in which a reactor is provided with a raw material supply port and a reaction gas outlet port can be used. The number of reaction tubes is not particularly limited, and either of a monotubular fixed bed reactor and a multitubular fixed bed reactor can be used, but a multitubular fixed bed reactor is preferably used. The internal diameter of this reaction tube is usually 10 to 40 mm and preferably 15 to 35 mm. In addition, a fixed bed reactor of heat-insulating system or heat-exchanging system can be used.

In the process of the present invention, a mixed gas containing methacrolein, isobutylene and oxygen and having a content of isobutylene of 300 to 3000 volume ppm is supplied to a reactor, and the oxidation is initiated so that the methacrolein conversion at an outlet of the reactor becomes at least 85%.

As the oxygen source, usually, the air is used. The mixed gas may contain an inert gas such as nitrogen, carbon dioxide, carbon monoxide, water vapor, or argon as a component other than methacrolein, isobutylene and oxygen [hereinafter, sometimes referred to as a different component]. Two or more of these inert gases may be contained, in addition, acetaldehyde, acetone, acrolein, acetic acid, acrylic acid, methacrylic acid, maleic acid, terephthalic acid and the like, which can be contained as impurities in raw materials to be used, may be contained in the mixed gas as long as the effect of the present invention is not impaired.

It is not necessarily required that methacrolein contained in the mixed gas is a purified product with high purity. For example, as methacrolein, a reaction gas containing methacrolein obtained, by a reaction of oxidizing isobutylene may be used without purification to high-purity methacrolein, the methacrolein may be unreacted methacrolein which is recovered from the reaction gas obtained after the reaction of oxidizing methacrolein, or may be a mixture of methacrolein obtained by the reaction of oxidizing isobutylene and unreacted methacrolein recovered from the reaction gas obtained after the reaction of oxidizing methacrolein.

Examples of the method of making the content of isobutylene in the mixed gas to 300 to 3000 volume ppm include (A) a method of preparing the mixed gas by adjusting the mixing ratio among methacrolein, isobutylene, oxygen and, optionally, a different component so that the content of isobutylene becomes 300 to 3000 volume ppm, (B) a method of obtaining a mixed gas containing methacrolein, isobutylene and oxygen by adjusting the content of isobutylene in a reaction gas containing methacrolein, unreacted isobutylene and unreacted oxygen at 300 to 3000 volume ppm, by adjusting the conversion of isobutylene in a reaction of oxidizing isobutylene, and (C) a method of mixing a reaction gas containing methacrolein and unreacted isobutylene obtained by a reaction of oxidizing isobutylene with at least one component selected from the group consisting of methacrolein, isobutylene, oxygen and, optionally a different component, so that the content of isobutylene becomes 300 to 3000 volume ppm, to obtain a mixed gas containing methacrolein, isobutylene, and oxygen. From the viewpoint of productivity, the method (B) or (C) is preferable, and the method (C) is more preferable. In the method (C), the content of isobutylene in the reaction gas containing methacrolein and unreacted isobutylene obtained by the reaction of oxidizing isobutylene can be adjusted by adjusting the conversion of isobutylene in the reaction of oxidizing isobutylene, and unreacted oxygen may be contained in the reaction gas. In the method (A) or (C), it is preferable to use the inert gas as an optionally contained different component.

The content of methacrolein in the mixed gas is preferably 2.5 to 5.0 volume %, and the molar ratio of oxygen relative to methacrolein is preferably 1 to 5. When water vapor is contained, the content of water vapor is preferably 1 to 30 volume %. The flow velocity of the mixed gas is as the space velocity of the mixed gas in the catalyst for producing methacrylic acid, preferably 500 to 5000 $h^{-1}$ based on the standard state tin terms of 0° C., 0.1 MPa). The space velocity can be obtained by dividing the amount of mixed gas passing through the reactor per hour (L/h) by the volume (L) of the catalyst for producing methacrylic acid in the reactor. The reaction temperature is usually 250 to 350° C., and the reaction pressure is usually 0.1 to 0.3 MPa.

The reaction of oxidizing isobutylene is performed by oxidizing isobutylene in the mixed gas containing isobutylene and oxygen, with oxygen, in the presence of the catalyst for producing methacrolein.

As the catalyst for producing methacrolein, a catalyst made of a complex oxide containing molybdenum, bismuth and iron is preferable. This catalyst can be produced by, for example, the methods disclosed in JP-A-59-46132, JP-A-60-163830, JP-A-2000-288396, and JP-A-2009-274034.

In the reaction of oxidizing isobutylene, methacrylic acid can be generated together with methacrolein, and generated methacrylic acid may be contained in the mixed gas containing methacrolein, isobutylene and oxygen.

The reaction of oxidizing isobutylene is performed by, for example, oxidizing isobutylene in a mixed gas containing isobutylene and oxygen, with oxygen, in a continuous manner, by extracting a reaction mixture from a reactor containing the catalyst for producing methacrolein, while supplying the mixed gas to the reactor.

As a reaction system in the reaction of oxidizing isobutylene, reaction systems such as a fluidized bed, a fixed bed, and a moving bed can be adopted, and it is desirable from the viewpoint of productivity and operability to perform the reaction by a fixed bed flowing system in which a mixed gas containing isobutylene and oxygen is flowed through the fixed bed reactor filled with the catalyst for producing methacrolein. A reaction by the fixed bed flowing system can be performed by for example, passing the mixed gas containing isobutylene and oxygen through the fixed bed reactor filled with the catalyst for producing methacrolein by upflow or downflow. In addition, as the fixed bed reactor, various fixed bed reactors of flowing system in which a reactor is provided with a raw material supply port and a reaction gas outlet port can be used. The number of reaction tubes is not particularly limited, and either of a monotubular fixed bed reactor and a multitubular fixed bed reactor can be used, but a multitubular fixed bed reactor is preferably used. The internal diameter of this reaction tube is usually 10 to 40 mm, and preferably 15 to 35 mm. In addition, a fixed bed reactor of heat-insulating system or heat-exchanging system can be used.

As an oxygen source in the reaction of oxidizing isobutylene, usually the air is used. A mixed gas containing isobutylene and oxygen may contain an inert gas such as nitrogen, carbon dioxide, carbon monoxide, water vapor, or argon as a component other than isobutylene and oxygen. In addition, two or more of these inert gases may be contained.

The content of isobutylene in the mixed gas containing isobutylene and oxygen is preferably 1 to 10 volume %, and the molar ratio of oxygen relative to isobutylene is preferably 1 to 3. When water vapor is contained, the content of water vapor is preferably 1 to 35 volume %. The flow velocity of the mixed gas is, as the space velocity of the mixed gas in the catalyst for producing methacrolein, preferably 500 to 5000 $h^{-1}$ based on the standard state (in terms of 0° C., 0.1 MPa). The space velocity can be obtained by dividing the amount of mixed gas passing through the reactor per hour (L/h) by the volume (L) of the catalyst for producing methacrolein in the reactor. The reaction temperature is usually 250 to 450° C., and the reaction pressure can be a reduced pressure, but is usually 0.1 to 0.5 MPa.

The content of isobutylene in a reaction gas obtained after the reaction of oxidizing isobutylene can be adjusted by the conversion of isobutylene, and as the conversion of isobutylene is higher, a reaction gas having a smaller content of isobutylene is obtained. The conversion of isobutylene can be regulated by, for example, adjusting the reaction temperature, and as the reaction temperature is higher, the conversion of isobutylene can be increased more.

In oxidation of methacrolein, since there is a tendency that the methacrolein conversion at the outlet of the reactor is increased as the reaction temperature is higher, the content of isobutylene in a mixed gas containing methacrolein, isobutylene and oxygen is smaller, the space velocity of methacrolein in the catalyst for producing methacrolein is smaller, or the amount of supply of oxygen to methacrolein is larger, methacrolein conversion (X1) at the outlet of the reactor at the time of initiation of oxidation (hereinafter, sometimes referred to as methacrolein initial conversion (X1)) should be made at least 85%, by adjusting at least one condition among them. The methacrolein initial conversion is preferably at least 90%, more preferably at least 95%, and further preferably at least 97%.

The reaction temperature in oxidation of methacrolein can be adjusted by adjusting the temperature of a temperature regulating means such as a heater, a jacket, or a heat medium bath included in the reactor. Here, the reaction temperature when the reaction is performed by a fixed bed flowing system is the temperature of a catalyst layer in a fixed bed reactor, and when the catalyst layer has a temperature distribution due to a local exothermic peak or the like, the reaction temperature is the lowest temperature of the catalyst layer, that is, the temperature of a portion having the lowest temperature in the catalyst layer. The fixed bed reactor is usually provided with a heat medium bath for temperature adjustment made of a nitrate of an alkali metal or the like. Since this heat medium temperature indicates the temperature or the lowest temperature of the catalyst layer, adjustment of the reaction temperature may be performed by adjusting this heat medium temperature. The temperature of the temperature regulating means is usually adjusted in the range of 250 to 350° C. The content of isobutylene in the mixed gas used in oxidation of methacrolein may be adjusted in the range of 300 to 3000 volume ppm by the aforementioned method. The space velocity of methacrolein the catalyst for producing methacrolein may be adjusted by regulating the content of methacrolein in the mixed gas used in oxidation of methacrolein, the supply amount of the mixed gas used in oxidation of methacrolein, or the like. The supply amount of oxygen relative to methacrolein may be adjusted by regulating the content of methacrolein and the content of oxygen in the mixed gas used in oxidation of methacrolein.

In the production of methacrylic acid, since the reaction of oxidizing methacrolein is an exothermal reaction, the amount of heat generation is increased in association with the supply amount of methacrolein. Upon initiation of production of methacrylic acid, if the supply amount of methacrolein is rapidly increased, there is a possibility that deterioration of the catalyst is caused due to heat generation. Particularly, when the reaction is performed by a fixed bed flowing system, since an excessive oxidation reaction occurs in a hot spot (abnormal local rise in temperature) generated in the catalyst layer, the yield is reduced in many cases and, further, since an excessive heat load is applied to the catalyst, the catalyst is deteriorated and the catalyst life may be reduced. For this reason, upon initiation of production of methacrylic acid, that is, upon startup, a method of increasing the methacrolein supply amount gradually or stepwisely is preferably adopted instead of rapidly increasing the supply amount to a predetermined methacrolein supply amount. Supply of a mixed gas containing methacrolein, isobutylene and oxygen and having a content of isobutylene of 300 to 3000 volume ppm into the reactor may be performed from the initiation of production of methacrylic acid, during increase to the predetermined methacrolein supply amount, or while maintaining a predetermined methacrylic acid supply amount after the amount has reached the predetermined methacrylic acid supply amount, that is, after the steady state has been realized. The period until the amount reaches the predetermined methacrylic acid supply amount is usually 1 to 300 hours, although it depends on the nature of the catalyst and other conditions.

After a mixed gas containing methacrolein, isobutylene and oxygen and having a content of isobutylene of 300 to 3000 volume ppm is supplied to a reactor and oxidation of methacrolein is initiated so that the methacrolein conversion at the outlet of the reactor becomes at least 85%, for example, when the oxidation is continued at a constant reaction temperature, as the reaction time passes, in other words, as the accumulated amount of treated methacrolein per catalyst unit weight is increased, the catalyst activity is gradually lowered and the methacrolein conversion at the outlet of the reactor is gradually reduced. Herein, continuation of the oxidation at a constant reaction temperature refers to continuation of oxidation of methacrolein so that the temperature is in the range of ±5° C. relative to the reaction temperature at the time of initiation of oxidation of methacrolein. In order to make the temperature in, the range of ±5° C. relative to the reaction temperature at the time of initiation of oxidation of methacrolein, adjustment should be performed as in the aforementioned adjustment of the reaction temperature in oxidation of methacrolein. It is preferable that continuation of oxidation of methacrolein at a constant reaction temperature is performed so that the temperature comes into the range of ±3° C. relative to the reaction temperature at the time of initiation of oxidation of methacrolein. When oxidation of methacrolein is continued at a constant reaction temperature, it is preferable that the reaction temperature therefor is in the range of 260 to 290° C.

In the process of the present invention, when the methacrolein oxidation is continued after the initiation thereof, the oxidation is continued while a mixed gas containing methacrolein, isobutylene and oxygen and having a content of isobutylene of 300 to 3000 volume ppm is supplied, until a difference (X1−X2) between methacrolein conversion (X2) at the outlet of the reactor and methacrolein initial conversion (X1) comes into the range of 2 to 30%, and the oxidation is continued while a mixed gas containing methacrolein, isobutylene and oxygen and having a content of isobutylene of 500 volume ppm or less is supplied, after the difference (X1−X2) has come into the range of 2 to 30%. That is, after the initiation of oxidation, the oxidation is continued while a mixed gas containing methacrolein, isobutylene and oxygen and having a content of isobutylene of 300 to 3000 volume ppm is supplied, a mixed gas containing methacrolein, isobutylene and oxygen to be supplied to a reactor is shifted to the mixed gas having a content of isobutylene of 500 volume ppm or less after methacrolein conversion (X2) at the outlet of the reactor is lowered from methacrolein initial conversion (X1) by 2% and until the methacrolein conversion (X2) is lowered by 30% and, thereafter, the oxidation is continued while a mixed gas containing methacrolein, isobutylene and oxygen and having a content of isobutylene of 500 volume ppm or less is supplied. As one example, when a mixed gas containing methacrolein, isobutylene and oxygen and having a content of isobutylene of 300 to 3000 volume ppm is supplied and the oxidation is initiated so that methacrolein initial conversion (X1) becomes 95%, it is advisable that the oxidation is continued while the mixed gas is supplied, and the mixed gas containing methacrolein, isobutylene and oxygen to be supplied to a reactor is shifted to the mixed gas having a content of isobutylene of 500 volume ppm or less after methacrolein conversion (X2) at the outlet of the reactor is lowered from methacrolein initial conversion (X1) by 2% and until the methacrolein conversion (X2) is lowered by 30%, that is, at the time when methacrolein conversion (X2) at the outlet of the reactor comes into the range of 93 to 65% and, thereafter, the oxidation is continued while the mixed gas having a content of isobutylene of 500 volume ppm or less is supplied.

However, the case is excluded where the oxidation is continued while a mixed gas containing methacrolein, isobutylene and oxygen and having a content of isobutylene of 300 to 500 volume ppm is supplied in both of the period until the difference (X1−X2) comes into the range of 2 to 30% after the initiation of oxidation and after the difference (X1−X2) comes into the range of 2 to 30%. That is, the case is excluded where the oxidation is continued while a mixed gas containing methacrolein, isobutylene and oxygen and having a content of isobutylene of 300 to 500 volume ppm is supplied all the time without shifting the mixed gas containing methacrolein, isobutylene and oxygen to be supplied to the reactor after the initiation of oxidation and until the difference (X1−X2) comes into the range of 2 to 30%, and after the difference (X1−X2) comes into the range of 2 to 30%.

Until the difference (X1−X2) comes into the range of 2 to 30% after the initiation of oxidation, the oxidation is continued while a nixed gas containing methacrolein, isobutylene and oxygen and having a content of isobutylene of 300 to 3000 volume ppm is supplied. Particularly when the mixed gas obtained by the method (B) or (C) is used during continuation of the oxidation, the content of isobutylene in the mixed gas containing methacrolein, isobutylene and oxygen to be supplied to the reactor may temporarily come out of the range of 300 to 3000 volume ppm for the reason such as failure of adjustment of isobutylene conversion, but there is no problem if such a case is temporary and the effect of the present invention is not impaired, and such a case is also included in the present invention. That is, it is sufficient if the oxidation is continued while a mixed gas containing methacrolein, isobutylene and oxygen and having a content of isobutylene of 300 to 3000 volume ppm is supplied for the most of time after the initiation of oxidation until the difference (X1−X2) comes into the range of 2 to 30%. Preferably, it is sufficient if a mixed gas containing methacrolein, isobutylene and oxygen and having a content of isobutylene of 300 to 3000 volume ppm is supplied for 90% or more of the time after the initiation of oxidation until the difference (X1−X2) comes into the range of 2 to 30%.

The content of isobutylene in a mixed gas containing methacrolein, isobutylene and oxygen to be supplied at the time of the initiation of oxidation and after the initiation of oxidation until the difference (X1−X2) comes into the range of 2 to 30% is preferably 300 to 2000 volume ppm.

In addition, in the process of the present invention, it is preferable that after the initiation of oxidation and until the difference (X1−X2) comes into the range of 5 to 20%, the oxidation is continued while a mixed gas containing methacrolein, isobutylene and oxygen and having a content of isobutylene of 300 to 3000 volume ppm is supplied, and after the difference (X1−X2) comes into the range of 5 to 20%, the oxidation is continued while a mixed gas containing methacrolein, isobutylene and oxygen and having a content of isobutylene of 500 volume ppm or less is supplied. It is more preferable that until the difference (X1−X2) comes into the range of 10 to 20%, the oxidation is continued while a mixed gas containing methacrolein, isobutylene and oxygen and having a content of isobutylene of 300 to 3000 volume ppm is supplied, and after the difference (X1−X2) comes into the range of 10 to 20%, the oxidation is continued while a mixed gas containing methacrolein, isobutylene and oxygen and having a content of isobutylene of 500 volume ppm or less is supplied.

Examples of the method of making the content of isobutylene in a mixed gas containing methacrolein, isobutylene and oxygen to 500 volume ppm or less include (D) a method of adjusting the mixing ratio among methacrolein, isobutylene, oxygen and, optionally, a different component so that the content of isobutylene becomes 500 volume ppm or less to prepare the mixed gas, (E) a method of adjusting the content of isobutylene in a reaction gas containing methacrolein, unreacted isobutylene and unreacted oxygen at 500 volume ppm or less by adjusting the conversion of isobutylene in a reaction of oxidizing isobutylene, to obtain a mixed gas containing methacrolein, isobutylene and oxygen, and (F) a method of mixing a reaction gas containing methacrolein and unreacted isobutylene obtained by a reaction of oxidizing isobutylene with at least one gas selected from the group consisting of methacrolein, isobutylene, oxygen, and an optionally contained different component, so that the content of isobutylene becomes 500 volume ppm or less, to obtain a mixed gas containing methacrolein, isobutylene and oxygen. The method (E) or (F) is preferable and the method (F) is more preferable in respect of productivity. In the method (F), the content of isobutylene in a reaction gas containing methacrolein and unreacted isobutylene obtained by a reaction of oxidizing isobutylene can be adjusted by adjusting the conversion of isobutylene in a reaction of oxidizing isobutylene, and unreacted oxygen may be contained in a reaction gas containing methacrolein and unreacted isobutylene. In the method (D) or (F), it is preferable to use the inert gas as an optionally contained different component. In the method (D), when the content of isobutylene in a mixed gas containing methacrolein, isobutylene and oxygen is set at 0 volume ppm, no isobutylene should be used. In the method (E), when the content of isobutylene in a mixed gas containing methacrolein, isobutylene and oxygen is set at 0 volume ppm, it is advisable that the conversion of isobutylene is made to be 100% and unreacted isobutylene is not contained in a reaction gas. In the method (F), when the content of isobutylene in a mixed gas containing methacrolein, isobutylene and oxygen is set at 0 volume ppm, it is advisable that the conversion of isobutylene is made to be 100% so that unreacted isobutylene is not contained in a reaction gas and isobutylene is not subjected to mixing with the reaction gas.

The content of isobutylene in a mixed gas containing methacrolein, isobutylene and oxygen to be supplied after the difference (X1–X2) comes into the range of 2 to 30% is preferably less than 300 volume ppm, and more preferably 10 volume ppm or more and less than 300 volume ppm.

After the difference (X1–X2) comes into the range of 2 to 30%, oxidation of methacrolein is continued while a mixed gas containing methacrolein, isobutylene and oxygen and having a content of isobutylene of 500 volume ppm or less is supplied to the reactor. Examples of the method therefor include (G) a method of continuing oxidation at a constant reaction temperature for a period in which a predetermined methacrolein conversion can be maintained, (H) a method of continuing oxidation until the temperature reaches a set upper limit temperature while gradually or stepwisely raising the reaction temperature, so that a predetermined methacrolein conversion can be maintained, (I) a method of continuing oxidation at a constant reaction temperature for a period in which a predetermined methacrolein conversion can be maintained, and then continuing oxidation until the temperature reaches a set upper limit temperature while gradually or stepwisely raising the reaction temperature, so that this predetermined methacrolein conversion can be maintained, and (J) a method of continuing oxidation until a set reaction condition is achieved by making a change in the reaction condition such as reduction in the space velocity of methacrolein in a catalyst for producing methacrolein or increase in the supply amount of oxygen relative to methacrolein, so that a predetermined methacrolein conversion can be maintained. The method (G) or (I) is preferable in respect of productivity. Herein, continuation of oxidation of methacrolein at a constant reaction temperature refers to continuation of oxidation of methacrolein an that the temperature is in the range of ±5° C., relative to the reaction temperature at the time of initiation of oxidation of methacrolein. In order to make the temperature in the range of ±5° C. relative to the reaction temperature at the time of the initiation of oxidation, adjust ent should be performed as in the aforementioned adjustment of the reaction temperature in oxidation of methacrolein. It is preferable that continuation of the oxidation at a constant reaction temperature is performed so that the temperature comes into the range of ±3° C. relative to the reaction temperature at the time of the initiation of oxidation. When oxidation of methacrolein is continued at a constant reaction temperature, it is preferable that the reaction temperature therefor in the range of 260 to 290° C. In the method (G) or (I), the predetermined methacrolein conversion is appropriately set according to the value of methacrolein initial conversion (X1) and the value of the difference (X1–X2), and for example, the conversion may be set in the range of 50 to 80%, and preferably set in the range of 65 to 75%. In the method (H) or (J), the predetermined methacrolein conversion is appropriately set according to the value of methacrolein initial conversion (X1) and the value of the difference (X1–X2), and for example, may be set in the range of 60 to 90%.

After the difference (X1–X2) comes into the range of 2 to 30%, oxidation of methacrolein is continued while a mixed gas containing methacrolein, isobutylene and oxygen and having a content of isobutylene of 500 volume ppm or less is supplied. During continuation of the oxidation, particularly when the mixed gas obtained by the method (E) or (F) is used, the content of isobutylene in a mixed gas containing methacrolein isobutylene and oxygen to be supplied to a reactor may temporarily come out of the range of 500 volume ppm or less for the reason such as failure of adjustment of isobutylene conversion, but there is no problem if such a case is temporary and the effect of the present invention is not impaired, and such a case is also included in the present invention. That is, it is sufficient if the oxidation is continued while a mixed gas containing methacrolein, isobutylene and oxygen and having a content of isobutylene of 500 volume ppm or less is supplied for the most of time after the difference (X1–X2) comes into the range of 2 to 30% and until continuation of the oxidation is completed. Preferably, it is sufficient if a mixed gas containing methacrolein, isobutylene and oxygen and having a content of isobutylene of 500 volume ppm or less is supplied for 90% or more of the time after the difference (X1–X2) comes into the range of 2 to 30% and until continuation of the oxidation is completed.

The process of the present invention can be adopted in combination with a method of reproducing a catalyst as described in JP-A-58-156351, JP-A-6-7885, JP-A-2000-191582 and JP-A-2003-306464, and thereby the period of use of a catalyst can be further extended. In this case, the process of the present invention may be applied upon initiation of operation using a new catalyst, upon resumption of operation using a reproduced catalyst, or upon both of them.

As the method of reproduction treatment, a method which can be performed with a catalyst filled in a reactor is preferable and, particularly, a method of performing heat treatment at 290 to 400° C. under the flow of a gas containing at least 3 volume % of oxygen and at least 3 volume % of water vapor is preferable, as described in JP-A-2003-306464.

Thus, durability of catalyst performance can be enhanced, and methacrylic acid can be produced with good productivity over a long period of time. Post-treatment operation of a gas generated in the reaction and containing the resulting methacrylic acid is appropriately selected, and examples thereof include a method of subjecting the gas to separation and purification operation after condensation or absorption of water. Recovered unreacted methacrolein can be recycled as a raw material, and an exhaust gas can be recycled as the inert gas source, optionally after being subjected to treatment such as burning.

EXAMPLES

The present invention will be specifically explained below by way of examples, but the present invention is not limited thereto.

In addition, the air and nitrogen used below contain substantially no moisture.

In each example, a mixed gas to be supplied to a reactor for producing methacrylic acid was analyzed by gas chromatography to obtain the content of isobutylene, the content of methacrolein, the content of oxygen and the content of water vapor in the mixed gas. In addition, the reaction mixture at the outlet of the reactor for producing methacrylic acid was analyzed by gas chromatography and the methacrolein conversion at the outlet of the reactor for producing methacrylic acid was calculated by the following equation.

Methacrolein conversion (%)=[(content of methacrolein in mixed gas to be supplied to reactor for producing methacrylic acid (mol))−(content of methacrolein in reaction mixture at outlet of reactor for producing methacrylic acid (mol))]/(content of methacrolein in mixed gas to be supplied to reactor for producing methacrylic acid (mol))×100

Reference Example 1

Preparation of Catalyst for Producing Methacrolein

In 1500 g of warm water, 13241 g of ammonium molybdate [$(NH_4)_6Mo_7O_{24} \cdot 4H_2O$] was dissolved, and this was named as A liquid. In 6000 g of warm water, 6060 g of iron (III) nitrate [$Fe(NO_3)_3 \cdot 9H_2O$], 1.3096 g of cobalt nitrate [$Co(NO_3)_2 \cdot 6H_2O$] and 585 g of cesium nitrate ($CsNO_3$), then, 2910 g of bismuth nitrate [$Bi(NO_3)_3 \cdot 5H_2O$] was dissolved, and this was named as B liquid. To the A liquid was added the B liquid while stirring the A liquid to obtain a slurry, which was subsequently spray-dried to obtain a dried material. To the resulting dried material was added 2.54 parts by mass of antimony trioxide [$Sb_2O_3$] based on 100 parts by mass of the dried material, which was molded into a ring having an external diameter of 6.0 mm, an internal diameter of 2.0 mm and a length of 6 mm together with 6 parts by mass of a silica alumina fiber (REC400-SL manufactured by ITM Co. Ltd.), and the ring was calcined at 543° C. for 6 hours under an air atmosphere to obtain a catalyst for producing methacrolein. The catalyst composition expect for oxygen was $Mo_{12}Bi_{0.96}Sb_{0.48}Fe_{2.4}Co_{7.2}Cs_{0.48}Si_{1.43}Al_{1.55}$.

Reference Example 2

Preparation of Catalyst for Producing Methacrylic Acid

In 224 kg of ion-exchanged water heated to 40° C. were dissolved 38.2 kg of cesium nitrate [$CsNO_3$], 24.2 kg of 85 wt % orthophosphoric acid, and 25.2 kg of 70 wt % nitric acid, and this was named as C liquid. On the other hand, in 330 kg of ion-exchanged water heated to 40° C. was dissolved 297 kg of ammonium molybdate tetrahydrate [$(NH_4)_6Mo_7O_{24}4H_2O$], 8.19 kg of ammonium metavanadate [$NH_4VO_3$] was suspended therein, and this was named as D liquid. The C liquid and the D liquid were adjusted to 40° C., the C liquid was added dropwise to the D liquid under stirring, and the mixture was stirred at 120° C. for 5.8 hours in a sealed vessel. Then, 10.2 kg of antimony trioxide [$Sb_2O_3$] and 10.2 kg of copper nitrate trihydrate [$Cu(NO_3)_2 \cdot 3H_2O$] were suspended in 23 kg of ion-exchanged water and added to the mixture, and this was stirred at 120° C. for 5 hours in a sealed vessel. The thus obtained slurry was dried with a spray drier. To 100 parts by weight of this dried powder were added 4 parts by weight of a silica alumina fiber [RFC400-SL, manufactured by ITM Co., Ltd.], 13 parts by weight of ammonium nitrate, and 9.7 parts by weight of ion-exchanged water, and the mixture was kneaded and extrusion-molded into a cylindrical shape having a diameter of 5 mm and a height of 6 mm. This molded product was dried at a temperature of 90° C. and a humidity of 30% RH for 3 hours, and held in the air stream at 220° C. for 22 hours, subsequently, at 250° C. for 1 hour to heat-treat the molded product, thereby, a catalyst precursor made of Keggin type heteropolyacid salt was obtained.

The temperature of the resulting catalyst precursor was raised to 390° C. in a stream of a mixed gas of the air and steam (moisture content: 1.4 volume %), and the precursor was held at the same temperature for 3 hours. Then, the air was switched with nitrogen, the temperature of the precursor was raised to 435° C. in a nitrogen stream, the precursor was calcined by being held, at the same temperature for 3 hours, and cooled to 70° C. in a nitrogen stream to obtain a catalyst for producing methacrylic acid. This catalyst for producing methacrylic acid was made of an acidic salt of Keggin type heteropolyacid containing phosphorus, molybdenum, vanadium, antimony copper and cesium at an atomic ratio of 1.5:12:0.5:0.5:0.3:1.4.

Example 1

Production of Methacrylic Acid

Into a reaction tube for producing methacrylic acid made of steel having an internal diameter of 25.4 mm provided with a heat medium bath was filled 1300 ml of the catalyst for producing methacrolein obtained in Reference Example 1, a raw material gas (A) prepared by mixing isobutylene, the air, steam and nitrogen was supplied to the reaction tube for producing methacrolein at a space velocity of 650 h$^{-1}$ (based on the standard state), and a reaction of oxidizing isobutylene was initiated at a reaction temperature of 350° C.

Into a reaction tube for producing methacrylic acid made of steel having an internal diameter of 25.4 mm provided with a heat medium bath was filled 1600 ml of the catalyst for producing methacrylic acid obtained in Reference Example 2, and supply of a mixed gas (B) prepared by mixing a reaction gas extracted from the outlet of the reaction tube for producing methacrolein by the reaction of oxidizing isobutylene, the air and nitrogen to the reaction tube for producing methacrylic acid was initiated at a space velocity of 550 h$^{-1}$ (based on the standard state) at the temperature of a heat medium for heating the reaction tube of 280° C. The supply amount of the mixed gas (B) was increased stepwisely over 8 hours from initiation of supply of the mixed gas (B) until the space velocity became 910 h$^{-1}$ (based on the standard state). The composition of the mixed gas (B) during the period of less than 8 hours from initiation of supply of the mixed gas (B) was methacrolein content: 0.7 to 3.3 volume %, oxygen content: 4.9 to 12.7 volume %, isobutylene content: 0 to 100 volume ppm, and water vapor content: 11.1 to 14.8 volume %, and the methacrolein conversion was fluctuated in the range of 98 to 100%. After 8 hours have passed from initiation of supply of the mixed gas (B), a mixed gas (C) (methacrolein content: 2.9 volume %, molecular oxygen content: 7.8 volume %, isobutylene content: 1600 volume ppm, water vapor content: 11.0 volume %) prepared by regulating the content of isobutylene in the resulting reaction gas by adjusting the isobutylene conversion of the reaction of oxidizing isobutylene and mixing the reaction gas, the air and nitrogen was supplied to the reaction tube for producing methacrylic acid in place of the mixed gas (B). When the methacrolein conversion upon switching with the mixed gas (C) was obtained by the aforementioned equation, the conversion was found to be 98%. In addition, during the period of 8 hours from initiation of supply of the mixed gas (B), the supply amount of the raw material gas (A) to be supplied to the reaction of oxidizing isobutylene was increased stepwisely to a space velocity of 1100 h$^{-1}$ (based on the standard state). During the period of 8 hours from initiation of supply of the mixed gas (B), the composition of the raw material gas (A) was such that the isobutylene content was 0.8 to 5 volume %, the molecular oxygen content was 5 to 13 volume %, the water vapor content was 7 to 35 volume %, and the isobutylene conversion was fluctuated in the range of 99.8 to 100%, and the reaction temperature in the reaction of oxidizing isobutylene was 345 to 350° C. The composition of the raw material gas (A) before initiation of supply of the mixed gas (C) after 8 hours have passed from initiation of supply of the mixed gas (B) was such that the isobutylene content was 4.2 volume %, the molecular oxygen write was 11 volume %, and the water vapor content was 8.9 volume %.

Production of methacrylic acid was performed by regulating the content of isobutylene in the resulting reaction gas by adjusting the isobutylene conversion of the reaction of oxidizing isobutylene for 1992 hours from initiation of supply of the mixed gas (C), supplying a mixed gas prepared by mixing the reaction gas, the air and nitrogen to a reaction tube for producing methacrylic acid under the condition of a temperature of a heat medium for heating a reaction tube for producing methacrylic acid of 280° C. and a space velocity of 910 $h^{-1}$ (based on the standard state) while the content of isobutylene in the mixed gas was made to be in the range of 302 to 1595 volume ppm. The content of methacrolein in the mixed gas supplied, to the reaction tube for producing methacrylic acid during the period of 1992 hours from initiation of supply of the mixed gas (C) was 2.8 to 3.2 volume %) the content of the molecular oxygen was 7.8 volume %, and the content of water vapor was 11.4 volume %. During the period of less than 1992 hours from initiation of supply of the mixed gas (C), the methacrolein conversion was fluctuated in the range of more than 85% to 98%, and when the methacrolein conversion was obtained by the aforementioned, equation after 1992 hours have passed from initiation of supply of the mixed gas (C), the conversion was found to be 85%, and the difference in methacrolein conversion from the methacrolein conversion at initiation of supply of the mixed gas (C) was 13% (=98%–85%).

After 1992 hours have passed from initiation of supply of the mixed gas (a), the mixed gas to be supplied to the reaction tube for producing methacrylic acid was switched with a mixed gas (D) (methacrolein content: 3.2 volume %, molecular oxygen content: 7.8 volume %, isobutylene content: 250 volume ppm, water vapor content: 110 volume %) prepared by mixing a reaction gas, in which the content of isobutylene had been regulated by adjusting the isobutylene conversion of the reaction of oxidizing isobutylene, the air and nitrogen. Thereafter, the mixed gas was supplied to the reaction tube for producing methacrylic acid under the condition of a temperature of a heat medium for heating a reaction tube for producing methacrylic acid of 280° C. and a space velocity of 910 $h^{-1}$ (based on the standard state) while the content of isobutylene in a mixed gas prepared by mixing the reaction gas, in which the content of isobutylene had been regulated likewise, the air and nitrogen was made to be in the range of 58 to 298 volume ppm, and production of methacrylic acid was continued. During the period of less than 3000 hours from initiation of supply of the mixed gas (D) (from 1992 hours after initiation of supply of the mixed gas (C) to less than 4992 hours), the methacrolein conversion was fluctuated in the range of more than 75% to 85%, and at the time when 3000 hours have passed from initiation of supply of the mixed gas (D) (4992 hours from initiation of supply of the mixed gas (C)), the methacrolein conversion at the outlet of the reactor was lowered to 75%. In addition, in the mixed gas which was supplied to the reaction tube for producing methacrylic acid during the period of 3000 hours after initiation of supply of the mixed gas (D) (from 1992 hours to 4992 hours after initiation of supply of the mixed gas (C)), the content of methacrolein was 2.8 to 3.6 volume %, the content of molecular oxygen was 7.8 volume % and the content of water vapor was 11.0 volume %. During the period of 4992 hours from initiation of supply of the mixed gas (C), the temperature of the heat medium for heating the reaction tube for producing methacrylic acid was 280° C. and the space velocity was 910 $h^{-1}$ (based on the standard state). In addition, during the period of 1992 hours from initiation of supply of the mixed gas (C), the composition of the raw material gas (A) was such that the content of isobutylene was 4.2 to 4.7 volume %, the content of molecular oxygen was 11 to 12 volume %, and the content of water vapor was 8.4 to 8.9 volume %, and the isobutylene conversion was fluctuated in the range of 96.0 to 99.2%, adjustment of isobutylene conversion was performed by regulating the reaction temperature of the reaction of oxidizing isobutylene, and the reaction temperature was between 323 to 334° C. The composition of the raw material gas (A) during the period of 3000 hours from initiation of supply of the mixed gas (D) was such that the content of isobutylene was 4.9 to 5.4 volume %, the content of molecular oxygen was 12.1 to 12.8 volume %, the content of water vapor was 7 to 8 volume %, the isobutylene conversion was fluctuated in the range of 99.4 to 99.8%, adjustment of isobutylene conversion was performed by regulating the reaction temperature of the reaction of oxidizing isobutylene, and the reaction temperature was in the range of 335 to 345° C.

Comparative Example 1

A reaction of oxidizing isobutylene was initiated by the same operation as that of Example 1, 1600 ml of the catalyst for producing methacrylic acid obtained in Reference Example 2 was filled into a reaction tube for producing methacrylic acid made of steel having an internal diameter of 25.4 mm provided with a heat medium bath, and supply of a mixed gas (E) prepared by mixing the reaction gas which had been extracted from the outlet of the reaction tube for producing methacrolein by the reaction of oxidizing isobutylene, the air and nitrogen to a reaction tube for producing methacrylic acid was initiated at a temperature of a heat medium for heating a reaction tube of 280° C. and a space velocity of 550 $h^{-1}$ (based on the standard state). The amount of supply of the mixed gas (E) was increased stepwisely until the space velocity became 910 $h^{-1}$ (based on the standard state) over 8 hours from initiation of supply of the mixed gas (E). Until less than 6 hours from initiation of supply of the mixed gas (E), the composition of the mixed gas (E) was such that the content of methacrolein was 0.7 to 3.3 volume %, the content of oxygen was 4.9 to 12.7 volume %, the content of isobutylene was 0 to 100 volume ppm, and the content of water vapor was 11.1 to 14.8 volume %, and the methacrolein conversion was fluctuated in the range of 98 to 100%. After 8 hours have passed from initiation of supply of the mixed gas (E), a mixed gas (F) (methacrolein content: 2.9 volume %, molecular oxygen content: 7.8 volume %, isobutylene content: 200 volume ppm, water vapor content: 11.0 volume %) prepared by regulating the content of isobutylene in the resulting reaction gas by adjusting the isobutylene conversion of the reaction of oxidizing isobutylene, and mixing the reaction gas, the air and nitrogen was supplied to the reaction tube for producing methacrylic acid, in place of the mixed gas (E). When the methacrolein conversion upon switching with the mixed gas (F) was obtained by the aforementioned equation, the conversion was found to be 98%. In addition, until 8 hours from initiation of supply of the mixed gas (E), the amount of supply of the raw material gas (A) to be supplied to the reaction of oxidizing isobutylene was increased stepwisely until the space velocity became 1100 $h^{-1}$ (based on the standard state). Until 8 hours have passed from initiation of supply of the mixed gas (E), the composition of the raw material gas (A)

was such that the isobutylene content was 0.8 to 5 volume %, the molecular oxygen content was 5 to 13 volume %, and the water vapor content was 7 to 35 volume % the isobutylene conversion was fluctuated in the range of 99.8 to 1.00%, and the reaction temperature in the reaction of oxidizing isobutylene was 345 to 350° C. The composition of the raw material gas (A) after 8 hours have passed from initiation of supply of the mixed gas (g) and before initiation of supply of the mixed gas (F) was such that the isobutylene content was 4.2 volume %, the molecular oxygen content was 11 volume %, and the water vapor content was 8.9 volume %.

While the content of isobutylene in the mixed gas prepared by regulating the content of isobutylene in the resulting reaction gas by regulating the isobutylene conversion of the reaction of oxidizing isobutylene after initiation of supply of the mixed gas (F), and mixing the reaction gas, the air and nitrogen was made to be in the range of 29 to 295 volume ppm, the mixed gas was supplied to the reaction tube for producing methacrylic acid under the condition of a temperature of a heat medium for heating a reaction tube for producing methacrylic acid of 280° C. and a space velocity of 910 $h^{-1}$ (based on the standard state), and production of methacrylic acid was continued. Until less than 4192 hours from initiation of supply of the mixed gas (F), the methacrolein conversion was fluctuated in the range of more than 75% to 98%, and at the time when 4192 hours have passed, the methacrolein conversion at the outlet of the reactor was lowered to 75%. In addition, in the mixed gas which was supplied to the reaction tube for producing methacrylic acid until 4192 hours from initiation of supply of the mixed gas (F), the methacrolein content was 2.8 to 3.6 volume %, the molecular oxygen content was 7.8 volume % and the water vapor content was 11.4 volume %. During the period of 4192 hours from initiation of supply of the mixed gas (F), the temperature of the heat medium for heating the reaction tube for producing methacrylic acid was 280° C. and the space velocity was 910 $h^{-1}$ (based on the standard state). In addition, the composition of the raw material gas (A) during the period of 4192 hours from initiation of supply of the mixed gas (F) was such that the isobutylene content was 4.2 to 5.4 volume % the molecular oxygen content was 11.0 to 12.8 volume %, and the water vapor content was 7.0 to 8.9 volume %, the isobutylene conversion was fluctuated in the range of 99.4 to 99.9%, adjustment of isobutylene conversion was performed by regulating the reaction temperature of the reaction of oxidizing isobutylene, and the reaction temperature was the range of 345 to 355° C.

What is claimed is:

1. A process for producing methacrylic acid comprising oxidizing methacrolein in a mixed gas containing methacrolein, isobutylene and oxygen, with oxygen, in a continuous manner, by extracting a reaction mixture from a reactor containing a catalyst for producing methacrylic acid, while supplying the mixed gas into the reactor, wherein the mixed gas having a content of isobutylene of 300 to 3000 volume ppm is supplied, and the oxidation is initiated so that the methacrolein conversion at an outlet of the reactor becomes at least 85%, thereafter, the oxidation is continued while the mixed gas having a content of isobutylene of 300 to 3000 volume ppm is supplied, until a difference (X1−X2) between methacrolein conversion (X2) at the outlet of the reactor and methacrolein conversion (X1) at the outlet of the reactor at the initiation of oxidation comes into the range of 2 to 30%, and the oxidation is continued while the mixed gas having a content of isobutylene of 500 volume ppm or less is supplied, after the difference (X1−X2) comes into the range of 2 to 30%, provided that the case is excluded where the oxidation is continued while the mixed gas having a content of isobutylene of 300 to 500 volume ppm is supplied, in both of the period until the difference (X1−X2) comes into the range of 2 to 30% from the initiation of oxidation, and after the difference (X1−X2) comes into the range of 2 to 30%.

2. The process according to claim 1, wherein the oxidation is performed so that the reaction temperature for a period during which the difference (X1−X2) comes into the range of 2 to 30% after the initiation of oxidation comes into the range of ±5° C. relative to the reaction temperature at the time of the initiation of oxidation.

3. The process according to claim 1, wherein the content of methacrolein in the mixed gas is 2.5 to 5.0 volume %.

4. The process according to claim 1, wherein the mixed gas is a reaction gas obtained by oxidizing isobutylene in a mixed gas containing isobutylene and oxygen, with oxygen, in the presence of a catalyst for producing methacrolein, or is a gas obtained by mixing said reaction gas with at least one gas selected from the group consisting of methacrolein, isobutylene, oxygen and an inert gas.

5. The process according to claim 1, wherein the reactor is a fixed bed reactor.

6. The process according to claim 1, wherein the catalyst for producing methacrylic acid is made of a heteropolyacid compound comprising phosphorus and molybdenum.

7. The process according to claim 6, wherein the heteropolyacid compound further comprises vanadium, at least one element selected from the group consisting of potassium, rubidium, cesium and thallium, and at least one element selected from the group consisting of copper, arsenic, antimony, boron, silver, bismuth, iron, cobalt, lanthanum and cerium.

8. The process according to claim 4, wherein the catalyst for producing methacrolein is made of a complex oxide containing molybdenum, bismuth and iron.

* * * * *